US012678088B2

(12) United States Patent
Yadav et al.

(10) Patent No.: US 12,678,088 B2
(45) Date of Patent: Jul. 14, 2026

(54) BRAIN WAVE CLASSIFICATION WITH BENEFICIAL ACTION RECOMMENDATIONS

(71) Applicant: Accenture Global Solutions Limited, Dublin (IE)

(72) Inventors: Rakesh Yadav, Pune (IN); Sanjoy Ghosh, Pune (IN); Trishika Basak, Kolkata (IN); Vikas Khurana, Pune (IN)

(73) Assignee: ACCENTURE GLOBAL SOLUTIONS LIMITED, Dublin (IE)

( * ) Notice: Subject to any disclaimer, the term of this patent is extended or adjusted under 35 U.S.C. 154(b) by 768 days.

(21) Appl. No.: 18/174,205

(22) Filed: Feb. 24, 2023

(65) Prior Publication Data

US 2024/0285220 A1 Aug. 29, 2024

(51) Int. Cl.
*A61B 5/369* (2021.01)
*A61B 5/00* (2006.01)
*G16H 50/20* (2018.01)

(52) U.S. Cl.
CPC ............ *A61B 5/369* (2021.01); *A61B 5/6803* (2013.01); *G16H 50/20* (2018.01)

(58) Field of Classification Search
CPC ....... A61B 5/369; A61B 5/6803; A61B 5/165; A61B 5/374; A61B 5/375; A61B 5/7267; G16H 50/20; G16H 50/70
See application file for complete search history.

(56) References Cited

U.S. PATENT DOCUMENTS

2015/0297109 A1* 10/2015 Garten ..................... A61B 5/38
600/28
2020/0388397 A1* 12/2020 Shoaran ................. A61B 5/725

FOREIGN PATENT DOCUMENTS

KR 20120106339 A * 9/2012 ........... A61B 5/7445

OTHER PUBLICATIONS

Ros et al., "PET Imaging of Dopamine Neurotransmission During EEG Neurofeedback", Frontiers in Physiology; Sec. Medical Physics and Imaging; Original Research, published Jan. 11, 2021; https://doi.org/10.3389/fphys.2020.5980503.
(Continued)

*Primary Examiner* — Jennifer Robertson
*Assistant Examiner* — Elina Sohyun Jang
(74) *Attorney, Agent, or Firm* — Mannava & Kang, P.C.

(57) ABSTRACT
Systems and methods for interpreting a user's brain wave data from EEGs using machine learning algorithms are described. In one example, a brain activity interpretation system classifies the EEG recording into five separate component signals, representing the five categories of brain waves (alpha, beta, theta, delta, gamma). In one example, the most dominant component signal is analyzed to determine whether the amplitude is higher or lower than an optimal range within the bandwidth for that brain wave. The system can then provide intelligent recommendations to the user for beneficial action(s) to help improve their everyday functioning and promote better regulation of their brain states. The system can help the user become more aware of their mental state and how to improve their mental state. EEG data is highly complex and unsuitable for immediate human comprehension, thus, the disclosed systems and methods improve the speed and accuracy of brain wave analysis.

18 Claims, 10 Drawing Sheets

(56) References Cited

OTHER PUBLICATIONS

Vakalopoulos, "The EEG as an index of neuromodulator balance i memory and mental illness", Frontiers in Neuroscience; Hypothesis and Theory Article, published Apr. 8, 2014; https://doi.org/10.3389/fnins.2014.00063.

* cited by examiner

300

310 — data_source - 2 col 2 col

320 — Numeric

330 — MeanImputer 1 col

340 — MaxAbsScaler

350 — LightGBMClassifier

400

BRAIN WAVE DATA —— 410

SELECET COLUMNS IN DATASET —— 420

440 —— MULTICLASS DECISION FOREST

SPLIT DATA —— 430

450 —— TRAIN MODEL

SCORE MODEL —— 460

EVALUATE MODEL —— 470

| BAND<br>510 | BRAIN<br>FREQUENCY<br>520 | TOO LOW -<br>RAISE ALERT<br>530 | TOO HIGH -<br>RAISE ALERT<br>540 | OPTIMAL<br>550 |
|---|---|---|---|---|
| | | PARAMETERS 500 | | |
| DELTA<br>WAVES | 0 Hz to 4 Hz | INABILITY TO<br>REVITALIZE THE<br>BRAIN, POOR<br>SLEEP | BRAIN INJURIES,<br>LEARNING PROBLEMS,<br>INABILITY TO THINK,<br>SEVERE ADHD | IMMUNE SYSTEM,<br>NATURAL HEALING,<br>RESTORATIVE / DEEP SLEEP |
| THETA<br>WAVES | 4 Hz to 8 Hz | POOR<br>EMOTIONAL<br>AWARENESS,<br>STRESS | ADHD, DEPRESSION,<br>HYPERACTIVITY,<br>IMPULSIVITY,<br>INATTENTIVENESS | CREATIVITY, EMOTIONAL<br>CONNECTION, INTUITION,<br>RELAXATION |
| ALPHA<br>WAVES | 8 Hz to 12 Hz | ANXIETY,<br>HIGH STRESS,<br>INSOMNIA,<br>OCD, PAIN | DAYDREAMING,<br>INABILITY TO FOCUS,<br>TOO RELAXED | RELAXATION |
| BETA<br>WAVES | 12 Hz to 40 Hz | ADHD,<br>DAYDREAMING,<br>DEPRESSION,<br>POOR COGNITION | ADRENALINE,<br>ANXIETY, HIGH<br>AROUSAL, INABILITY<br>TO RELAX, STRESS | CONSCIOUS FOCUS,<br>MEMORY, PROBLEM<br>SOLVING |
| GAMMA<br>WAVES | 40 Hz to 100 Hz | ADHD,<br>DEPRESSION,<br>LEARNING<br>DISABILITIES | ANXIETY,<br>HIGH AROUSAL,<br>STRESS | BINDING SENSES, COGNITION,<br>INFORMATION PROCESSING,<br>LEARNING, PERCEPTION,<br>REM SLEEP |

FIG. 5

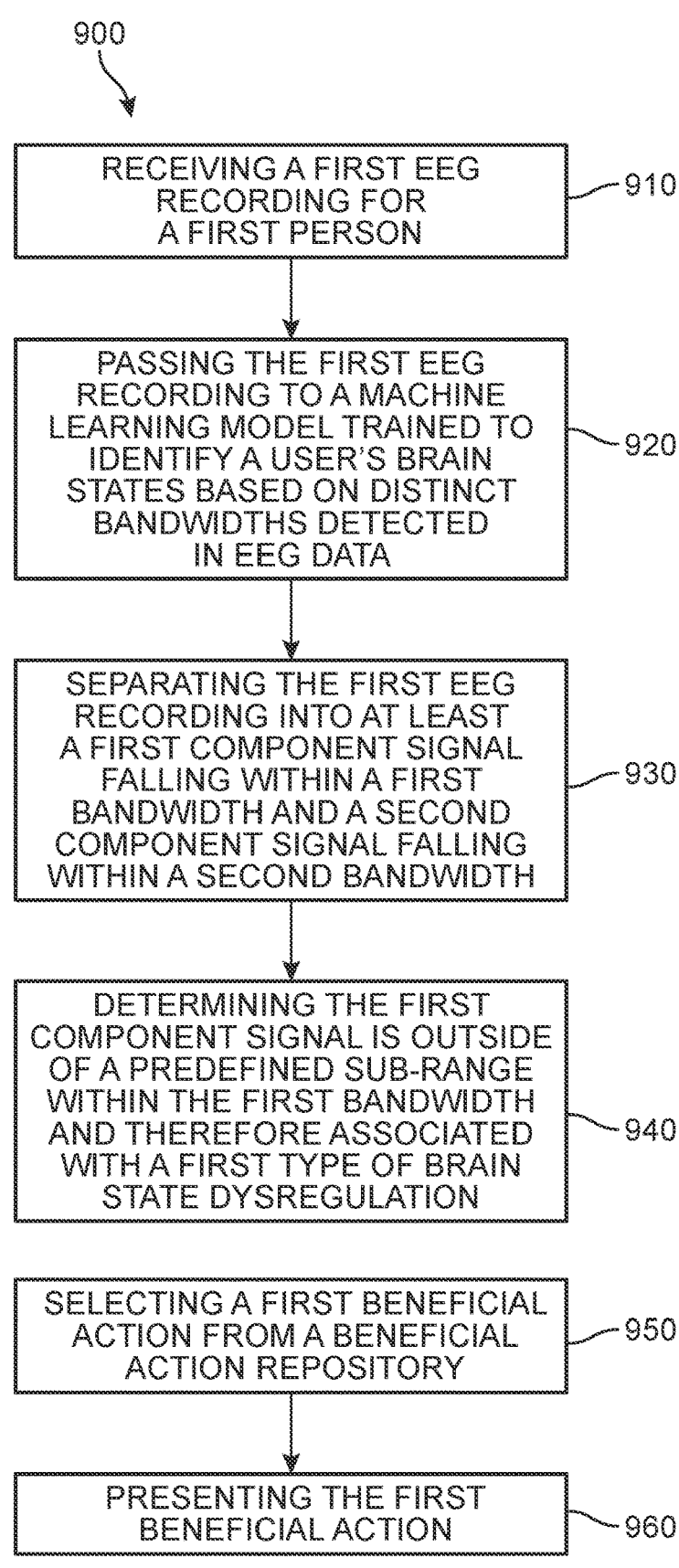

900

RECEIVING A FIRST EEG
RECORDING FOR
A FIRST PERSON                     910

PASSING THE FIRST EEG
RECORDING TO A MACHINE
LEARNING MODEL TRAINED TO
IDENTIFY A USER'S BRAIN
STATES BASED ON DISTINCT
BANDWIDTHS DETECTED
IN EEG DATA                        920

SEPARATING THE FIRST EEG
RECORDING INTO AT LEAST
A FIRST COMPONENT SIGNAL
FALLING WITHIN A FIRST
BANDWIDTH AND A SECOND
COMPONENT SIGNAL FALLING
WITHIN A SECOND BANDWIDTH          930

DETERMINING THE FIRST
COMPONENT SIGNAL IS OUTSIDE
OF A PREDEFINED SUB-RANGE
WITHIN THE FIRST BANDWIDTH
AND THEREFORE ASSOCIATED
WITH A FIRST TYPE OF BRAIN
STATE DYSREGULATION                940

SELECTING A FIRST BENEFICIAL
ACTION FROM A BENEFICIAL
ACTION REPOSITORY                  950

PRESENTING THE FIRST
BENEFICIAL ACTION                  960

1010 — PROCESSOR

1012 — MEMORY

1014 — BRAIN ACTIVITY INTERPRETATION SYSTEM

1018 — PREPROCESSING MODULE

1020 — MODEL TRAINING & DEVELOPMENT

1022 — MACHINE LEARNING BANDWIDTH CLASSIFICATION MODEL

1024 — INTELLIGENT RECOMMENDATION ENGINE

1004

1006

NETWORK

1002

1008

1090

BRAIN WAVE CLASSIFICATION WITH BENEFICIAL ACTION RECOMMENDATIONS

TECHNICAL FIELD

The present disclosure generally relates to the field of brain signal analysis. More specifically, the present disclosure generally relates to the use of predictive models to classify brain wave data and neurotransmitter activity and to recommend a corresponding beneficial action to better promote a person's well-being. The output of the system can be used in various fields, such as in the area of medical sciences like neurological research, physiological research, and clinical neurological disease diagnosis, as well as sports, behavior, neurological research, neural function enhancement, sleep assessments, pain management, and treatment for addiction or detoxification.

BACKGROUND

When neurons are activated, they produce electrical pulses. By placing electrodes on the scalp, the electrical activity of the brain, known as electroencephalogram (EEG), can be recorded. In turn, EEG is generated by a specific type of synchronous activity of neurons which are known as pyramidal neurons and the electrical output is thus reflected in the following areas of the skin where the electrodes are located. Different patterns of electrical activity, known as brain waves, could be recognized by their amplitudes and frequencies. Frequency indicates how fast the waves oscillate which is measured by the number of waves per second (Hz), while amplitude represents the power of these waves measured by microvolt (UV). It is theorized that certain attributes of mental state or thought processes may in fact be determined through passive monitoring, such as EEG, with some degree of statistical reliability. It should be understood, however, that such EEG data is highly complex and unsuitable for immediate human comprehension.

There is a need to discover and describe relationships between neural patterns and well-being that yield improved sensory and emotional feedback systems. Further research on ways to characterize and recognize physiological states and brain states that correlate with different levels of well-being. There is also a need to develop improved data-based intervention and training programs to enable humans to reach greater potentials. It is further desirable to provide end-users with a mechanism by which to readily comprehend their own baseline brain states and learn strategies for improving their physical and mental health.

There is a need in the art for a system and method that addresses the shortcomings discussed above.

BRIEF DESCRIPTION OF THE DRAWINGS

The invention can be better understood with reference to the following drawings and description. The components in the figures are not necessarily to scale, emphasis instead being placed upon illustrating the principles of the invention. Moreover, in the figures, like reference numerals designate corresponding parts throughout the different views.

FIG. 5 is a table showing a decision tree with parameters that can be used for classification, according to an embodiment;

FIG. 9 is a flow chart depicting a method of interpreting brain wave data for medical research, diagnosis, or behavioral therapy, according to an embodiment.

SUMMARY

Figure 1:
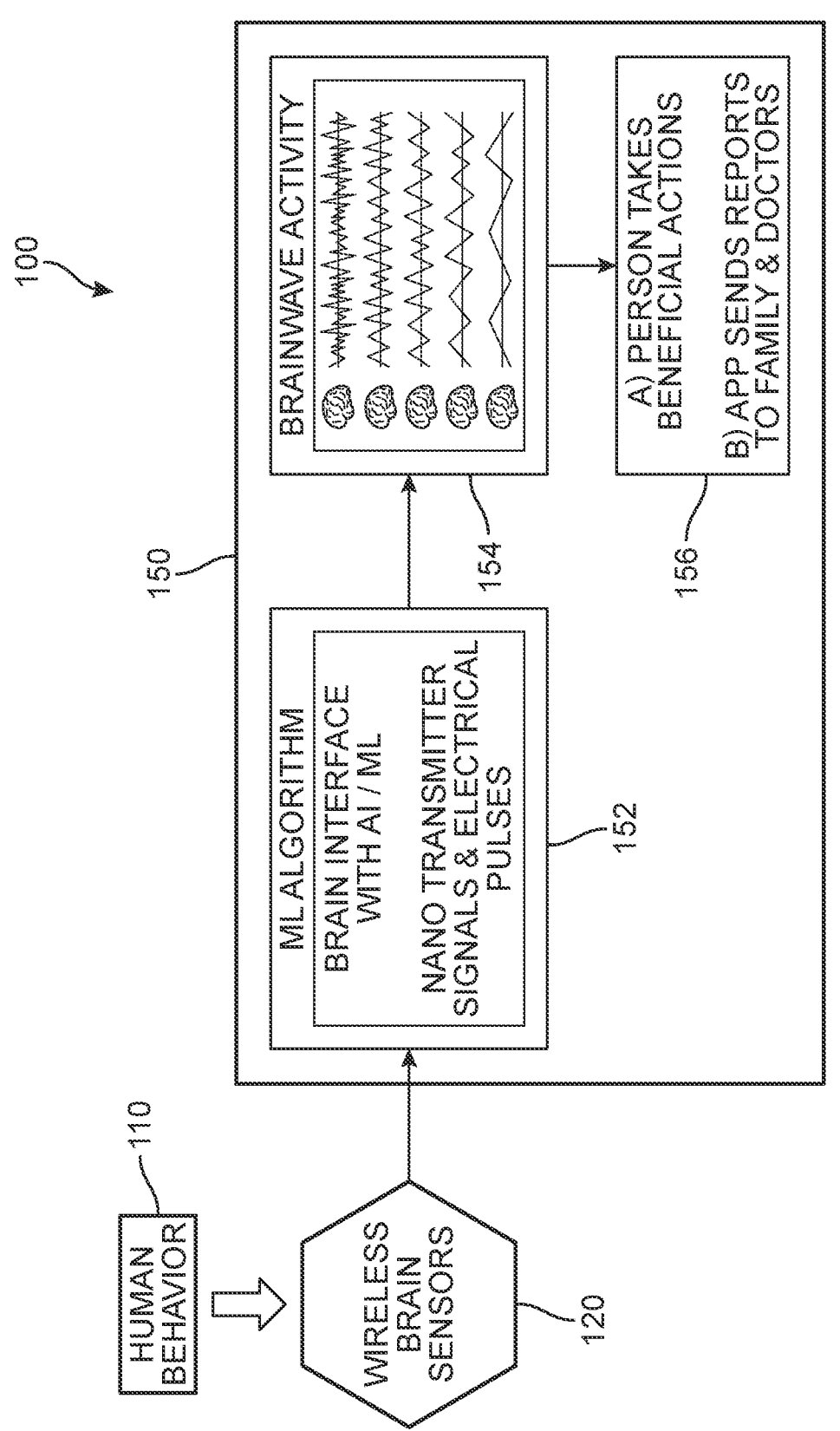
FIG. 1 is a schematic diagram of a high-level overview of a brain activity interpretation framework, according to an embodiment.

Implementations described herein provide for a brain activity interpretation system that incorporates a trained machine learning (ML) model that can classify brain wave data into distinct component signals. The brain wave data can include EEG recordings taken from a human via a set of electrodes that represent electrical activity of the brain. In one example, the EEG recording is decomposed to isolate and classify the five types of waveforms recognized in brain activity, including alpha, beta, gamma, theta, and delta waves. The dominant component signal is analyzed and used to evaluate the person's brain state (e.g., cognitive and/or affective state). In some embodiments, based on this classification and analysis, the system can automatically present beneficial actions to help the user improve their brain state.

In one aspect, the disclosure provides a computer-implemented method for interpreting brain wave data for medical research, diagnosis, or behavioral therapy. The method includes a first step of receiving, at a brain activity interpretation system, a first electroencephalogram (EEG) recording for a first person. The EEG recording can be initially received as a raw data file that is pre-processed to extract the EEG recording. In a second step, the method includes passing the first EEG recording as input to a machine learning model of the brain activity system, the machine learning model being trained to identify a user's brain states based on distinct bandwidths detected in EEG data. A third step includes separating (and outputting), via the machine learning model, the first EEG recording into at least a first component signal falling within a first bandwidth and a second component signal falling within a second bandwidth that differs from the first bandwidth, and a fourth step includes determining, at the brain activity interpretation system, the first component signal is outside of a predefined sub-range within the first bandwidth and therefore associated with a first type of brain state dysregulation. In addition, a fifth step includes selecting, at the brain activity interpretation system and based on the first type of brain state dysregulation, a first beneficial action from a beneficial action repository, and a sixth step includes presenting, via a dashboard for the brain activity interpretation system, the first beneficial action.

In another aspect, the disclosure provides a non-transitory computer-readable medium storing software comprising instructions executable by one or more computers which, upon such execution, cause the one or more computers to interpret brain wave data for medical research, diagnosis, or behavioral therapy by performing the following: (1) receive, at a brain activity interpretation system, a first electroencephalogram (EEG) recording for a first person; (2) pass the first EEG recording as input to a machine learning model of the brain activity system, the machine learning model trained to identify a user's brain states based on distinct bandwidths detected in EEG data; (3) separate (and output), via the machine learning model, the first EEG recording into at least a first component signal falling within a first bandwidth and a second component signal falling within a second bandwidth that differs from the first bandwidth; (4) determine, at the brain activity interpretation system, the first component signal is outside of a predefined sub-range within the first bandwidth and therefore associated with a first type of brain state dysregulation; (5) select, at the brain activity interpretation system and based on the first type of brain state dysregulation, a first beneficial action from a beneficial action repository; and (6) present, via a dashboard for the brain activity interpretation system, the first beneficial action.

In another aspect, the disclosure provides a system for interpreting brain wave data for medical research, diagnosis, or behavioral therapy. The system comprises one or more computers and one or more storage devices storing instructions that are operable, when executed by the one or more computers, to cause the one or more computers to: (1) receive, at a brain activity interpretation system, a first electroencephalogram (EEG) recording for a first person; (2) pass the first EEG recording as input to a machine learning model of the brain activity system, the machine learning model trained to identify a user's brain states based on distinct bandwidths detected in EEG data; (3) separate (and output), via the machine learning model, the first EEG recording into at least a first component signal falling within a first bandwidth and a second component signal falling within a second bandwidth that differs from the first bandwidth; (4) determine, at the brain activity interpretation system, the first component signal is outside of a predefined sub-range within the first bandwidth and therefore associated with a first type of brain state dysregulation; (5) select, at the brain activity interpretation system and based on the first type of brain state dysregulation, a first beneficial action from a beneficial action repository; and (6) present, via a dashboard for the brain activity interpretation system, the first beneficial action.

Other systems, methods, features, and advantages of the disclosure will be, or will become, apparent to one of ordinary skill in the art upon examination of the following figures and detailed description. It is intended that all such additional systems, methods, features, and advantages be included within this description and this summary, be within the scope of the disclosure, and be protected by the following claims.

While various embodiments are described, the description is intended to be exemplary, rather than limiting, and it will be apparent to those of ordinary skill in the art that many more embodiments and implementations are possible that are within the scope of the embodiments. Although many possible combinations of features are shown in the accompanying figures and discussed in this detailed description, many other combinations of the disclosed features are possible. Any feature or element of any embodiment may be used in combination with or substituted for any other feature or element in any other embodiment unless specifically restricted.

This disclosure includes and contemplates combinations with features and elements known to the average artisan in the art. The embodiments, features, and elements that have been disclosed may also be combined with any conventional features or elements to form a distinct invention as defined by the claims. Any feature or element of any embodiment may also be combined with features or elements from other inventions to form another distinct invention as defined by the claims. Therefore, it will be understood that any of the features shown and/or discussed in the present disclosure may be implemented singularly or in any suitable combination. Accordingly, the embodiments are not to be restricted except in light of the attached claims and their equivalents. Also, various modifications and changes may be made within the scope of the attached claims.

DESCRIPTION OF EMBODIMENTS

The proposed systems and methods are directed to data analysis using machine learning models with the goal of accurately predicting an individual person's brain wave frequencies. The model can classify the brain wave to determine which neurotransmitters are most likely to be affecting the individual at a given time. The electroencephalogram (EEG) is one of the oldest non-invasive investigative tools of brain neurophysiology. It measures summed electrical currents generated by neural activity from multiple scalp electrode sites. The EEG measures changes in activity on a temporal scale unmatched by more modern imaging techniques, often in the range of only a few seconds. While conventional approaches have offered methods by which to interpret of EEG findings, the significance of this electrical activity in relation to cognitive function still remains relatively opaque. Typically, EEG data has been assessed in conjunction with functional imaging such as functional magnetic resonance imaging (fMRI) and positron emission tomography (PET) scanning, which have poor temporal, but better spatial resolution, in an attempt to identify the underlying brain processes. However, it can be appreciated that such scanning techniques involves a much greater investment of time, machine access, and processing power than the data collected via EEG. The ability to rely primarily on EEG data—which can be readily and more affordably collected using portable devices—to accurately determine a user's cognitive and emotional states would represent a significant advance in research and individual insights into brain activity.

It can be appreciated that there is an intimate relationship between neurotransmitter action within a given network of neurons and the electrical features resulting from it. Neurotransmitters are chemical molecules or messengers which enable transfer of information across the body and deliver messages. There are multiple neurotransmitters, including Dopamine, Serotonin, and Norepinephrine, among others, and each neurotransmitter plays a distinct and powerful role within the brain for day-to-day functioning of the brain and body as well as basic emotional responses.

Neurotransmitters act on the molecular level by receptor interaction—in other words, a neuron integrates a series of excitatory and inhibitory events associated with the various neurotransmitters when identifying whether it should "fire"

or not. Modulation of different neurotransmitter levels have been shown to modulate the release of other neurotransmitters, which are then also reflected in the brain's electrical signals. Hence, the electrical activity of a neuronal network can be understood to represent a high-level representation of the chemical transmitters active in the brain at the same time. Thus, the electrical signals associated with these neurotransmitters are rich in brain activity information and are an important means of brain research, physiological research, and clinical brain disease diagnosis.

As will be described in greater detail below, the proposed embodiments provide translation or interpretation of data collected via a wide variety of sensor devices. In one embodiment, the system incorporates trained machine learning (ML) algorithms that can classify brain wave data for individual persons. The output of the system can be used in various fields, such as in the area of medical sciences like neurological research, physiological research, and clinical neurological disease diagnosis, as well as sports, behavior, neurological research, neural function enhancement, sleep assessments, pain management, and treatment for addiction or detoxification.

For example, the proposed model can incorporate insights developed from studies that describe a link between neurotransmitter activity and several well-described EEG rhythms. In other words, there may be specific and interpretable qualitative and quantitative changes in the EEG that reflect cognition and its dysfunction, which can be representative of specific neurotransmitter activity. As one specific and non-limiting example, it has been observed that inverse neuromodulation of widespread cortical networks is finely tuned to the effects of two main classes of neurotransmitter, acetylcholine (ACh) and the monoamines serotonin, dopamine, and noradrenaline. Indeed, cholinergic modulation has been noted to heavily affect both cognition and affect. Imbalances of monoaminergic and cholinergic signaling are key attributes of the major sleep stages that can be associated with depression, and these are reflected in and defined by EEG rhythms. Furthermore, memory consolidation, including aspects of implicit and explicit memory, have been observed as having a direct relationship to cholinergic and monoaminergic neuromodulation.

As general background for the reader, it can be understood that the electrical activity of a neuronal network represents a high level of integration which is situated in between the biochemical molecular basis of communication and behavior. It is therefore very meaningful to pick up this electrical activity in order to create a link between the biochemical base of neurotransmitter action on a molecular level and the desired effects on mood and well-being. Local electrical activity in the depth of the brain—referred to as a field potential—is reflected in the electroencephalogram (EEG), as can be obtained from the scalp in humans. Analysis of brain field potentials or electrical power recorded as EEG has been proven to be a very sensitive tool to characterize drug effects on the central nervous system. For example, the electrical power or dominance of single frequency ranges may change independently from each other depending on the particular behavioral or drug condition. Thus, following a drug application, the pattern of changes of the brain field potential with respect to these specially defined frequency ranges can serve as an "electrical fingerprint" that shows the brain activity for a person when specific types or amounts of neurotransmitters or other drugs are present. Therefore, there is strong evidence to support the concept of a close relationship between specific defined EEG frequency ranges and neurotransmitter action. This physiological interpretation of EEG frequencies could help to develop and detect more receptor specific drugs but also might be used to interpret the correlations between human behaviors (including behavior that is conducive to well-being, such as exercise, meditation, sleep, listening to calming or soothing music or other audio, and behavior that is disruptive to well-being, such as sedentary lifestyles, stress, lack of sleep, etc.) and different EEG frequencies in each bandwidth. Such correlations can provide valuable insights that can be used to generate insights and feedback for each user.

Brain patterns form wave shapes that are commonly sinusoidal. Usually, they are measured from peak to peak and normally range from 0.5 to 100 $\mu$V in amplitude. In one example, a power spectrum from the raw EEG signal can be derived. In the power spectrum, the contribution of sine waves with different frequencies are visible. Although the spectrum is continuous, ranging from 0 Hz up to one half of sampling frequency, the brain state of the individual may make certain frequencies more dominant, a factor that is used by the machine learning model to determine a person's most likely brain state.

Different frequency components are categorized into delta (less than 4 Hz), theta (4-8 Hz), alpha (8-12 Hz), beta (12-40 Hz), and gamma (40-100 Hz) where each represents a particular physiological function. However, it should be understood that while these ranges are known in the field of neuroscience, the actual EEG signal carrying the component signals can be processed in a way so as to take into account of normal uncertainty that may accompany the raw data (e.g., variability in sensor device equipment, individual human scalp noise, etc.). For purposes of this application, the model can be configured to isolate each of the five bandwidths with a range variation of 5%, and in some cases, up to 10-15%, as per standard neurological research practices.

As a very high-level summary, delta waves are typically observed in the EEG signal when a person is asleep, theta waves when a person is sleepy, alpha waves when a person is relaxed and his/her muscles are loose but he/she is awake, beta waves when a person is alert, and gamma waves are observed when a person is trying to solve a problem. Alpha activity is typically induced by closing the eyes and by relaxation, and abolished by eye opening or alerting by any mechanism (thinking, calculating). Most humans are sensitive to the phenomenon of "eye closing", i.e., when they close their eyes their wave pattern significantly changes from beta into alpha waves. EEG is thus sensitive to a continuum of brain states ranging from stress state, alertness to resting state, hypnosis, and sleep. During normal state of wakefulness with open eyes beta waves are dominant. In relaxation or drowsiness the power of alpha activity rises and if sleep appears, the power of lower frequency bands increase.

For purposes of this application, a person's "brain state" refers to patterns of correlation between brain waves, or an objectively discernable and quantifiable pattern of power density, neuronal firing, correlations between brain waves, and/or other dynamic physical characteristics of the brain. As used in this application, brain states can be statistically defined and reflect a relationship with a "cognitive state" or "mental state" (or affective state) label. These brain states can be observed during conscious, subconscious and/or sleep stages. For example, a "brain state" may be characterized by the functional coordination of the connectivity and coherent phase-amplitude coupling between a brain's delta, theta, alpha, gamma, and beta frequency waves.

Referring now to FIG. 1, an overview of the proposed embodiments is depicted. As shown in FIG. 1, a brain state management framework 100 can collect data 110 related to a user's brain waves via one or more sensors 120 (e.g., electrodes). The data 110 can be passed to a machine learning classification model 152 of a brain activity interpretation system ("system") 150, which can analyze the data associated with the frequency ranges detected and generate insights 154 based on these electrical pulses regarding the person's neurotransmitter activity. In some embodiments, the system 150 can further select one or more specific beneficial actions 156 (also referred to herein as "interventions") that are recommended for promotion of the user's well-being as well as a detailed report summarizing the data analysis for the benefit of the user, their medical professionals, and/or family.

Figure 2:
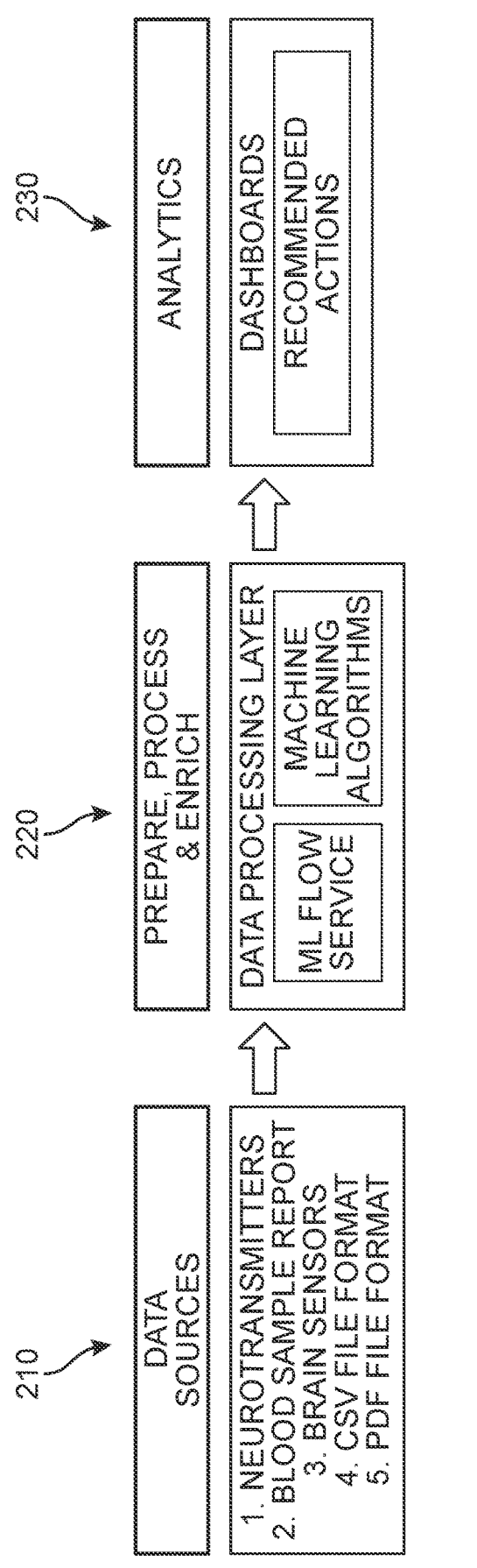
FIG. 2 is a schematic diagram of a process by which a data for a person can be analyzed to identify dysregulated brain wave patterns, according to an embodiment.

It can be appreciated that in different embodiments, the proposed systems can incorporate information beyond that of EEGs. For example, referring to FIG. 2, the brain activity interpretation system can receive and process data from sources 210 such as neurotransmitter test results (e.g., such as a baseline test panel can be taken that provides data on 11 key neurotransmitters and precursors: glutamate, epinephrine, norepinephrine, dopamine, phenylethylamine, gamma-aminobutyric acid (GABA), serotonin, glutamine, histamine, glycine and taurine, etc.), blood samples, urine samples, other types of brain sensor data. Such data can be collected in various file formats (e.g., txt, csv, pdf, excel, etc.). In some embodiments, a sensor device such as an EEG cap or other biometric sensor may be associated with a user, and may include one or more biometric sensors configured to capture data, e.g., biometric data, indicative of a physiological state of a user. In some examples, the sensor device can include or be connected to additional components that store the captured biometric data and transmit portions of captured biometric data to a data processing layer 220 of the system at various time intervals.

As one non-limiting example, a sensor device may detect and capture data of a user identifying heart rate, respiration rate, blood pressure, body temperature, skin conductance, electrical activity of their brain (e.g., characterized by EEG data). In some embodiments, other physiological and biomechanical characteristics can be received by the system, such as a rate of blinking, metrics indicative of posture, metrics indicative of a position of their head, data characterizing sleep patterns, and/or accelerometer or gyroscopic data characterizing a motion of their body. Furthermore, as some examples, a sensor device may include, but is not limited to, a wearable device, a smart watch or wristband (e.g., an Apple Watch™ or a Fitbit™ wristband), a portable EEG unit/cap and associated system, an optical head-mounted display unit (e.g., Google Glass™ or other smart-glasses), smart fabrics having embedded electrical and sensor components (e.g., Sensoria™ socks or other wearable smart devices), and any additional or alternate communications device, such as a smart phone, capable of capturing biometric data characterizing a user's physiological state and transmitting that biometric data to the brain activity interpretation system.

In different embodiments, the data can be collected while the user is involved in a range of tasks, and/or at different times of the day. For example, while at work, a person may require different levels of physical exertion and mental awareness in contrast to when the same person is at home relaxing. In some embodiments, the data can be stored for comparison with future data, and/or to determine a baseline. In one example, the system can store the received, detected, or derived portions of biometric data within one or more structured data records of a data repository, such as biometric database for the user.

In some embodiments, the system can apply analytical processes that may include one or more machine learning algorithms, one or more algorithmic or research-based techniques, and one or more probabilistic techniques, such as data mining techniques and other techniques that analyze and leverage "big data." The applied machine learning algorithms, algorithmic or research-based techniques, and/or probabilistic techniques may detect time-varying patterns and generate output data indicative of the detected patterns.

In some embodiments, the data processing layer 220 can classify the features in the data using an ML algorithm that implements deterministic classification models. In one embodiment, the ML algorithm is configured to filter or isolate two or more individual sub-signals associated with alpha, beta, theta, gamma, delta bandwidths. At any given time, all of these (five) waves are present in the EEG signal, but some of will be expressing with greater power than the others, corresponding to the most dominant brain wave at that time. The separation of the larger EEG signal into these multiple component signals allows the model to monitor the activity of the user in these distinct ranges, and assess the user's brain state with far more comprehensiveness and richer, low-level detail. The model's subsequent analysis can then be based on parsed or segregated data that has been classified based on its bandwidth category. With this bandwidth-specific information, the ML algorithm can be used to assess the user' level of stress, physical or mental fatigue, or a level of alertness or focus, which can be presented in a dashboard via an analytic module 230 of the system (e.g., see FIG. 5). In different embodiments, the ML algorithm can analyze portions of the stored biometric data captured by the sensor device(s) or other data collection apparatuses during a prior time period, a current time period, and/or in real-time to identify time-varying brain activity patterns in a user's physiological state during these prior time periods and to predict biometrics characteristics during one or more future time periods. For example, the biometric characteristics may include, but are not limited to levels of stress, fatigue, mental focus, and other physical or mental manifestations of user physiological state.

In other words, embodiments of the system incorporate a predictive model implements a set of rules which identify, and then classify, the brain wave data. In different embodiments, the model is able to process the data and then further enhance the data to that would help in the classification. Thus, EEG data can be fed into the model and distinguish the overlapping frequencies that are being simultaneously produced by the brain (i.e., the model can filter and/or separate the bandwidths from the single EEG signal) so that the data becomes useful and can support intelligent beneficial actions based on the one or two most dominant bandwidth(s) having the most power in the EEG signal.

In some embodiments, biometric input data from data sources 210 may include measurements of a user's brain wave activity captured by a sensor device at regular intervals (e.g., every 5, 10, 15, 30, 60 minutes). The data processing layer 220 can apply the one or more machine learning algorithms to predict user brain states. As some illustrative examples, the application of the machine-learning algorithms may indicate that a user's alpha wave patterns are lower than normal between 5:00 p.m. and 5:30 a.m., which can be associated with anxiety, stress, insomnia, obsessive compulsive disorder (OCD), and/or pain, or the user's gamma wave patterns are higher than normal from 9:30 am to 10:30 am, coinciding with a daily meeting, and associated with anxiety, high arousal, and stress. Based on these detected trends, and optionally on the additional stored data characterizing user levels of stress, fatigue, and mental focus, the machine learning algorithm may establish trends that can be used to intelligently select recommendations for presentation to the user (e.g., via an interactive user interface dashboard).

As another example, if the detected brain wave patterns indicate that, between 6:15 a.m. and 10:30 a.m., the user's levels of stress and fatigue are at a low level, and their level of focus is at a high level, the analytic module 230 can select one or more recommendations that promote performance of complex, high-risk tasks. In contrast, if the detected brain wave patterns indicate that, between 10:50 a.m. and 1:00 p.m., the same user's levels of stress and fatigue are at a high level, and their level of focus is at a low level, the analytic module 230 may select one or more recommendations to performance of tasks with little or no complexity or risk. Further, analytic module 230 can suggest beneficial actions, such as adjusting their nutritional intake at lunch, meditation or taking a walk after lunch, or refraining from writing emails or engaging in communications that require an emotional investment from the user.

Figure 3:
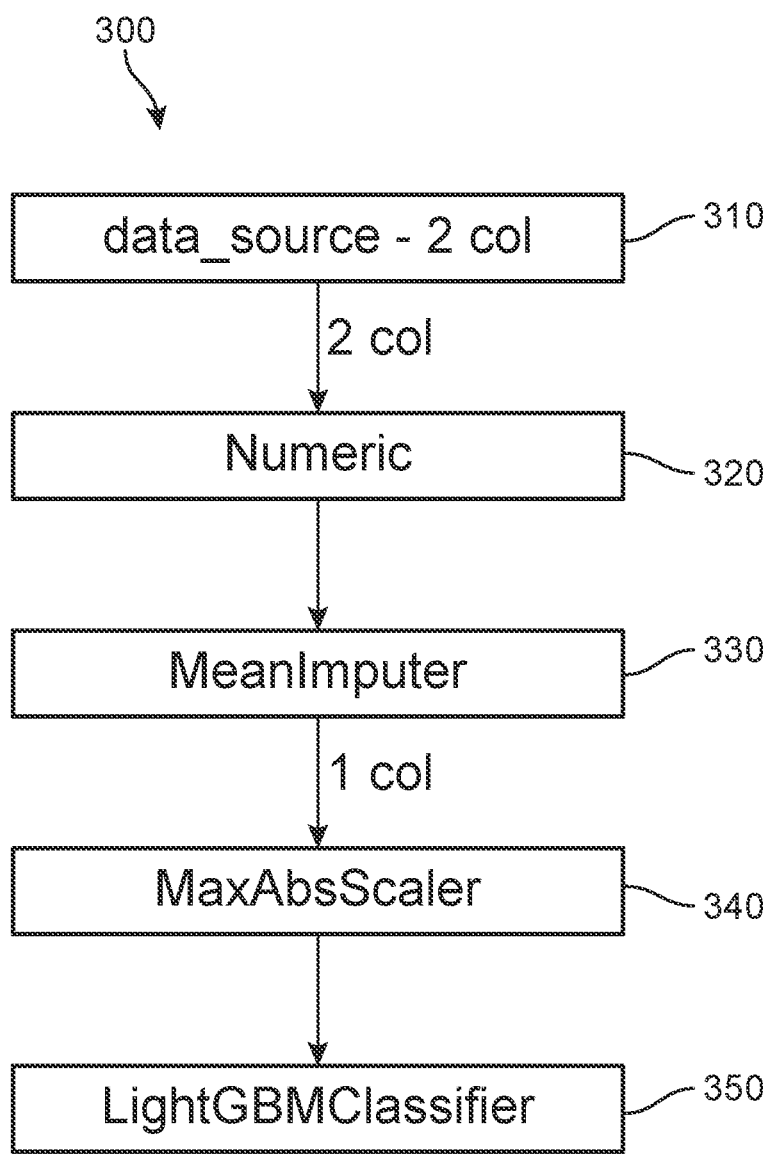
FIG. 3 is a flow diagram showing a data transformation process performed on EEG data, according to an embodiment.

Moving now to FIG. 3, a flow diagram depicting one example of a data transformation process 300 that may be used by the proposed embodiments is provided. In a first stage 310, raw data (including decimal values) from a data source is received. It can be appreciated that this raw data is highly complex and unreadable for human comprehension. In other words, the data cannot be interpreted into meaningful/actionable insights without the implementation of the models and computing techniques as described herein. In some embodiments, the data can then be pre-processed and arranged as two columns of numeric values (segregated) in a second stage 320. For example, data samples (in the form of a dataset file) are prepared and preprocessed to transform the data to a format that can be parsed by the machine.

In a third stage 330, the numeric values are passed through a mean imputation processor to produce an output of one column. For example, a MeanInputer estimator can be used to fill in the missing values in the dataset as part of the data preprocessing. In some embodiments, one or more feature engineering techniques (e.g., Azure Machine Learning studio) is implemented to select the most relevant features in the dataset.

A fourth stage 340 involves applying a scaling technique (in this case, MaxAbsScaler) to the one column of mean values to enrich the data, thereby preparing the data to be leveraged by the model before analysis occurs. This step scales the data to its maximum value; that is, it divides every observation by the maximum value of the variable. In one example, the result of the preceding transformation is a distribution in which the values vary approximately within the range of −1 to 1. For example, the scaling technique can scale and translate the feature values to convert the data into a more manageable feature expression range. The technique can be applied individually to each of the five bandwidths in the EEG signal. In other embodiments, different scaling techniques such as MinMaxScaler, RobustScaler, Standard-Scaler, Absolute Maximum Scaling, Normalization, and Standardization can be used, among other scaling techniques. The scaled data is then passed to a light gradient-boosting machine (LightGBM) classifier in a fifth stage 350. LightGBM is a gradient boosting framework that uses tree-based learning algorithms. It is designed to be distributed and efficient and, based on multiple trials, was found to offer a faster training speed and higher efficiency with lower memory usage than other classifiers. However, in other embodiments, different classification techniques can be used, including XGBoost, tensorflow.rb, Rumale, CatBoost, SciKitLearn, Random Forest, or other gradient tree boosting techniques.

Figure 4:
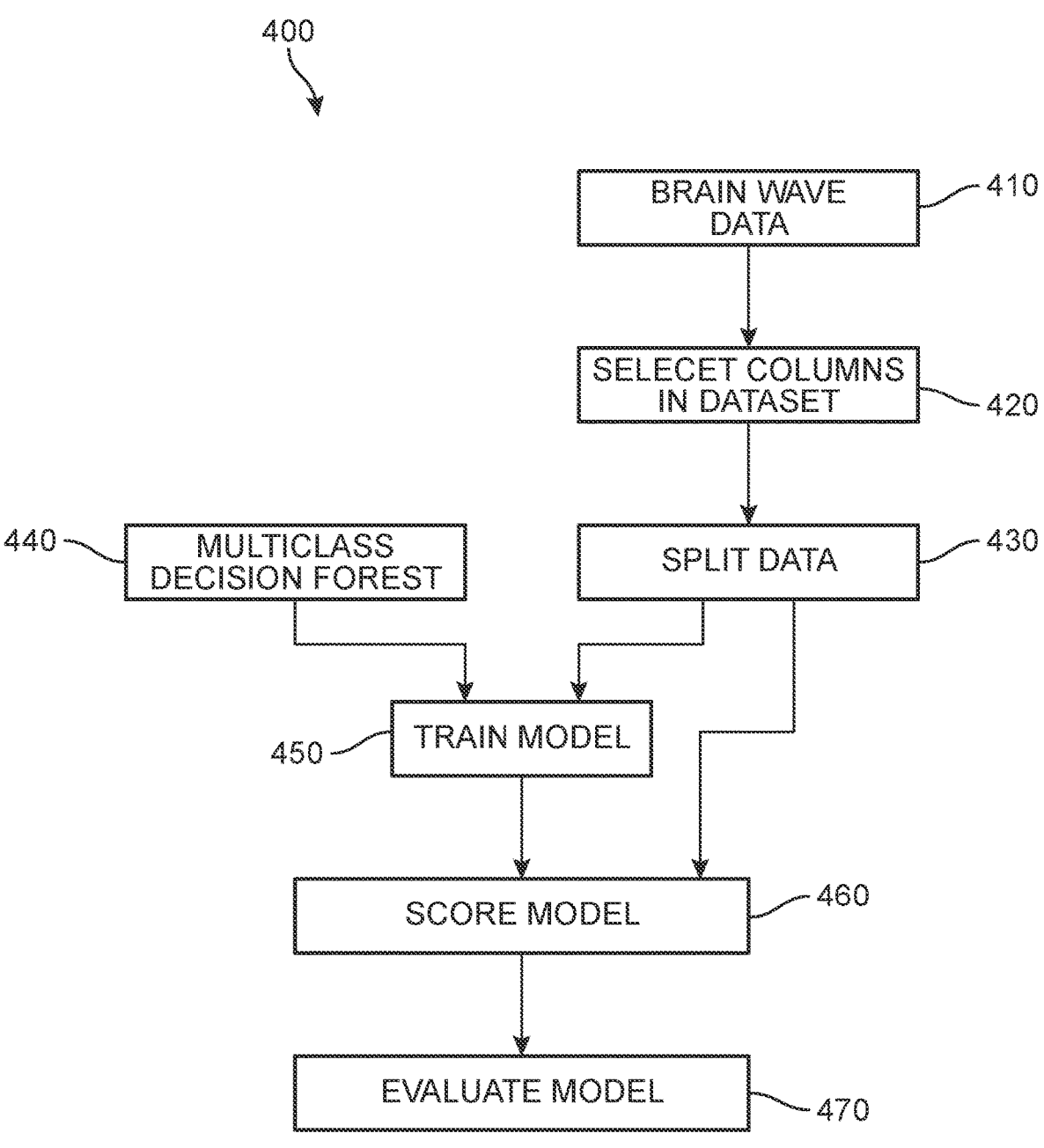
FIG. 4 is a flow diagram showing a process of interpreting brain wave data using a machine learning model, according to an embodiment.

FIG. 4 presents a flow diagram of an embodiment of a model training process 400. In different embodiments, training of the ML models may be performed until the artificial intelligence correctly identifies the user's brain states at a predetermined threshold (e.g., based on feedback from the user and/or people interacting with the user). For example, some embodiments may include testing the ML model against data sets to verify that the model is working well or accurately. In some embodiments, the parameters may include Hidden Markov Model parameters and the model may be a Hidden Markov Model. In some embodiments, the parameters may include Convolutional Neural Network parameters and the model may be a Convolutional Neural Network. In some embodiments, the parameters may include Recurrent Neural Network parameters and the model may be a Recurrent Neural Network.

In FIG. 4, as brain data is received in a first stage 410, columns are selected in the dataset in a second step 420, and then split in a third stage 430. The split data, along with data from a multiclass decision forest (e.g., see FIG. 5) in a fourth stage 440, is used to train the model in a fifth stage 450. The trained model is used to generate scores in a sixth stage 460, and the model is then evaluated in a seventh stage 470. In trials testing the model's performance, it was observed that the majority of the model metrics (e.g., area under curve (AUC), F1-weighted score, precision score, weighted accuracy, etc.) demonstrated that the model was performing with acceptable accuracy. Thus, the model was able to provide the classification of brain states for each data range.

An example of a set of decision tree parameters that may be used for classification with some of the proposed embodiments is presented in FIG. 5. As a general matter, decision trees typically operate using a flowchart structure, where each feature is represented by an internal node, data is split by branches, and each leaf node represents the outcome. It is a kind of "white box" supervised machine learning algorithm, meaning all partitioning logic is accessible.

The table in FIG. 5 presents a set of parameters related to the frequency band of brain wave activities. More specifically, for each band 510, a corresponding brain frequency 520 is listed, as well as brain state characteristics when the frequency for a particular band is too low 530, too high 540, and optimal 550. Thus, it can be seen that humans can experience variations in their brain frequencies, but when those variations are significant or extreme (high or low) within a particular bandwidth, there may be a cause for concern. These extremes within a given bandwidth can be linked to specific physical symptoms or poor functioning cognitive and/or emotional states.

Figure 6:
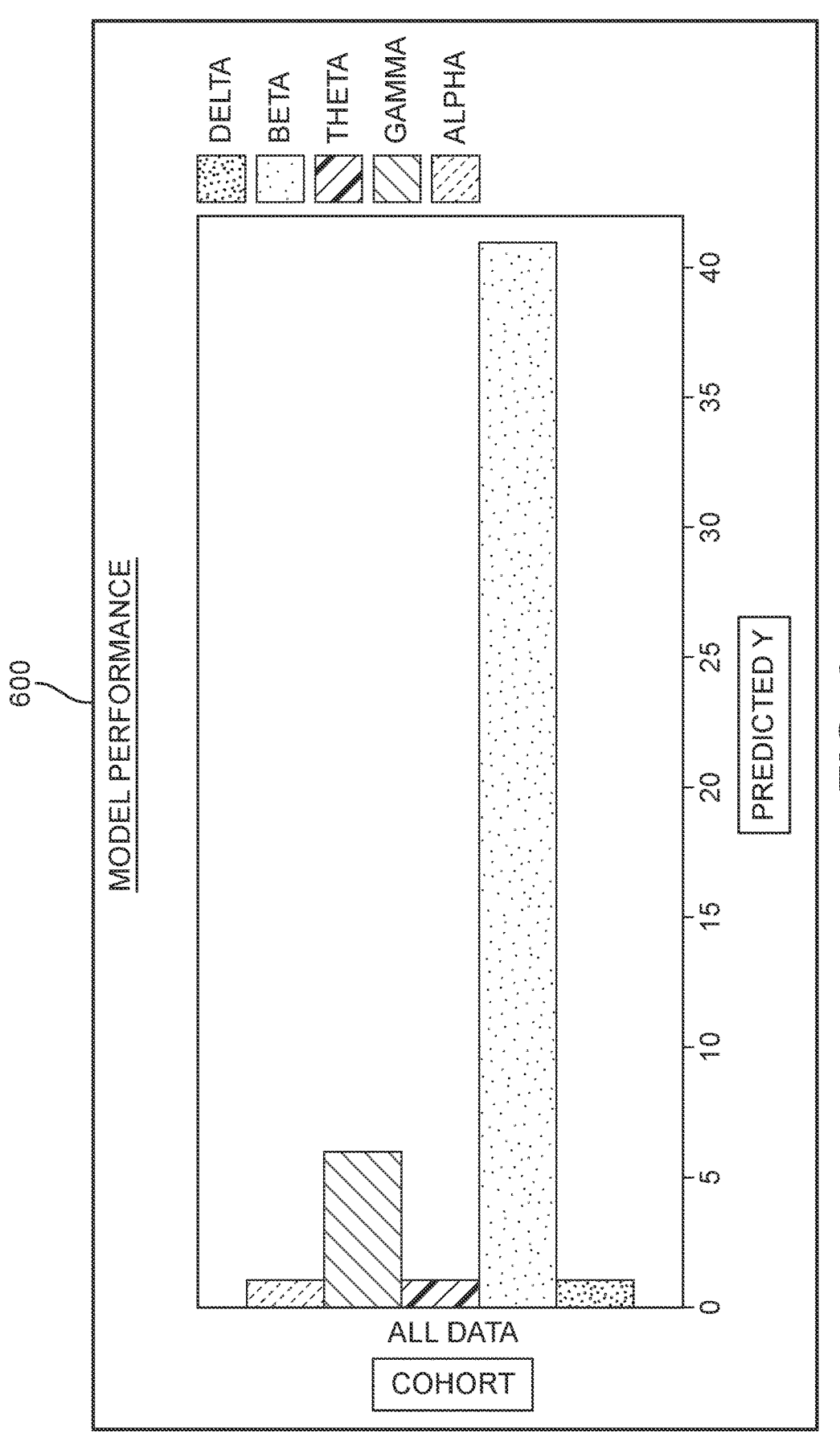
FIG. 6 is an example of an output of the machine learning model, according to an embodiment.

For purposes of reference, one example of a model output 600 (shown here as a bar graph) is depicted in FIG. 6. The model output represents the brain activity for a person over a period of time. In the graph, a legend indicates the brain wave bandwidths that were assessed by the model, including Delta, Beta, Theta, Gamma, and Alpha. For purposes of this example, the model has identified the highest brainwave activity as falling in the Beta bandwidth, with a value of approximately 41 Hz. The remaining brain activity was classified with a second highest value of 6 for Gamma, and the remaining bands (Delta, Alpha, Theta) having approximately the same value of 1. Thus, for the tested person, over the given time period, their brain activity is primarily exhibiting Beta waves, with some Gamma activity.

With this information, the model can further determine the specific frequency range of the Beta and Gamma waves. If the Beta waves for the person are determined to fall on the low end of the 12 Hz to 40 Hz segment, the person may be susceptible to symptoms such as attention-deficit/hyperactivity disorder (ADHD), daydreaming, depression, and/or poor cognition. If, on the other hand, the Beta waves for the person are determined to fall toward the high end of the 12 Hz to 40 Hz segment, the person may be susceptible to symptoms such as high adrenaline, anxiety, arousal, stress, and/or an inability to relax. However, if the Beta waves for the person are determined to fall along the middle of the 12 Hz to 40 Hz segment (optimal), the person may be better adapted to engaging in activities with conscious focus, better memory, and improved problem solving. Additional brain state characteristics can also be inferred by the model based on the specific Gamma waves, though these would weigh as heavily in the person's brain state based on the current data. Thus, there may be some partial (not as significant as those indicated by the Beta waves) effects if the Gamma waves fall on the low end of the 40 Hz to 100 Hz segment, the person may be susceptible to symptoms such as ADHD, depression, and learning disabilities; if the Gamma waves fall on the higher end of the 40 Hz to 100 Hz segment, the person may be susceptible to symptoms such as anxiety, high arousal, and stress; and if the Gamma waves fall toward a center of the 40 Hz to 100 Hz segment, the person may be susceptible to symptoms such as improved cognition, information processing, learning, perception, rapid eye movement (REM) sleep, and binding/incorporation of senses.

Figure 7:
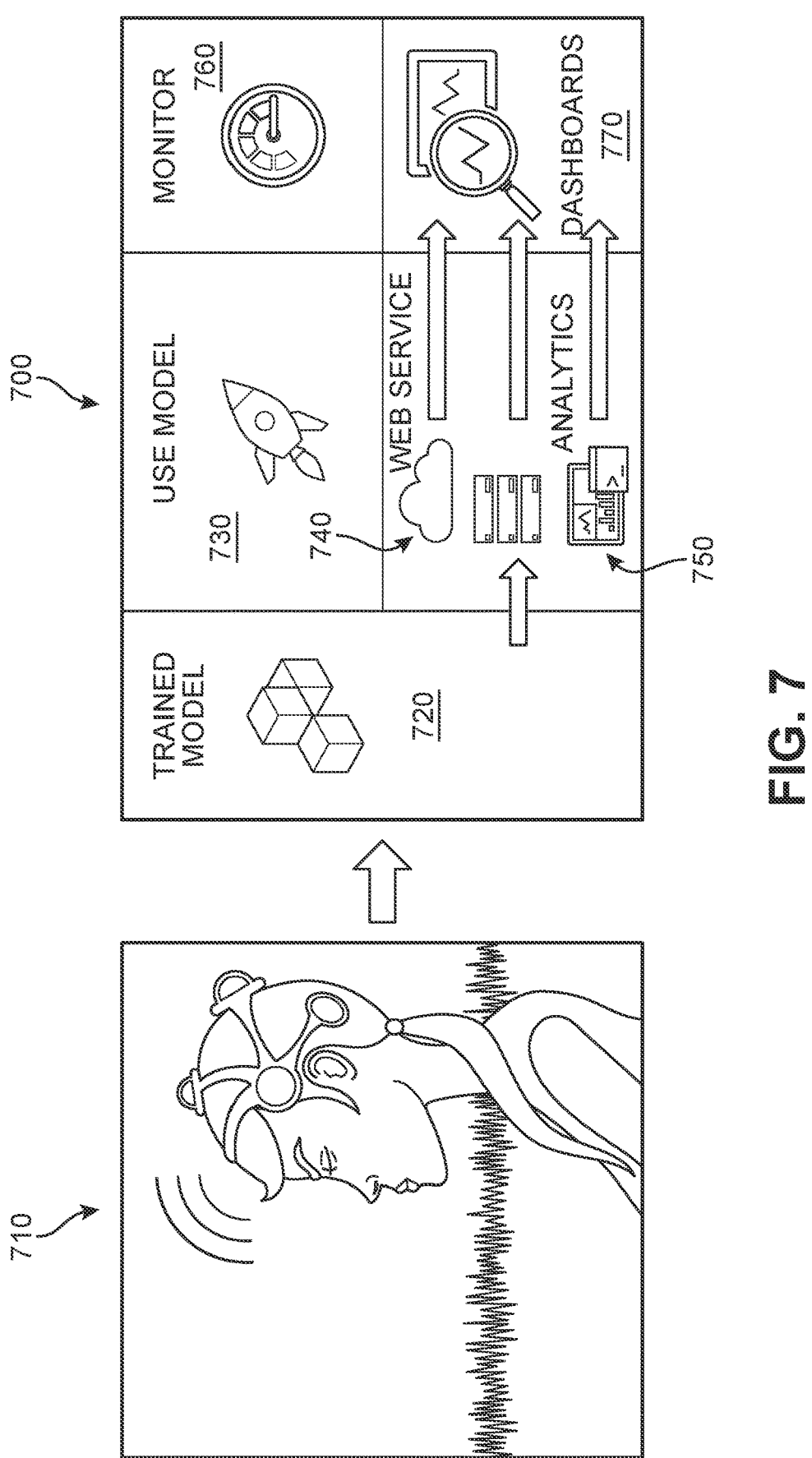
FIG. 7 is a depiction of a data collection session for a user, according to an embodiment.

FIG. 7 depicts an example of a data collection session 710 where a user 712 provides brain data 718 via a head-mounted sensor device 714 for transmission over a network 716 to an embodiment of a brain activity interpretation system 700. Once the user's brain data 718 is received by a trained model 720, the model can perform classification and predictive analysis on the data and provide monitoring 760 of the user's brain state(s). In some embodiments, the brain data 718 is also stored at a data repository, where past brain activity and current brain activity can be used to generate analytics 750 for presentation at a user dashboard 770. In some embodiments, the data ingestion process and/or dashboard 770 can be provided as part of a web service 740 accessible via a cloud server.

Figure 8:
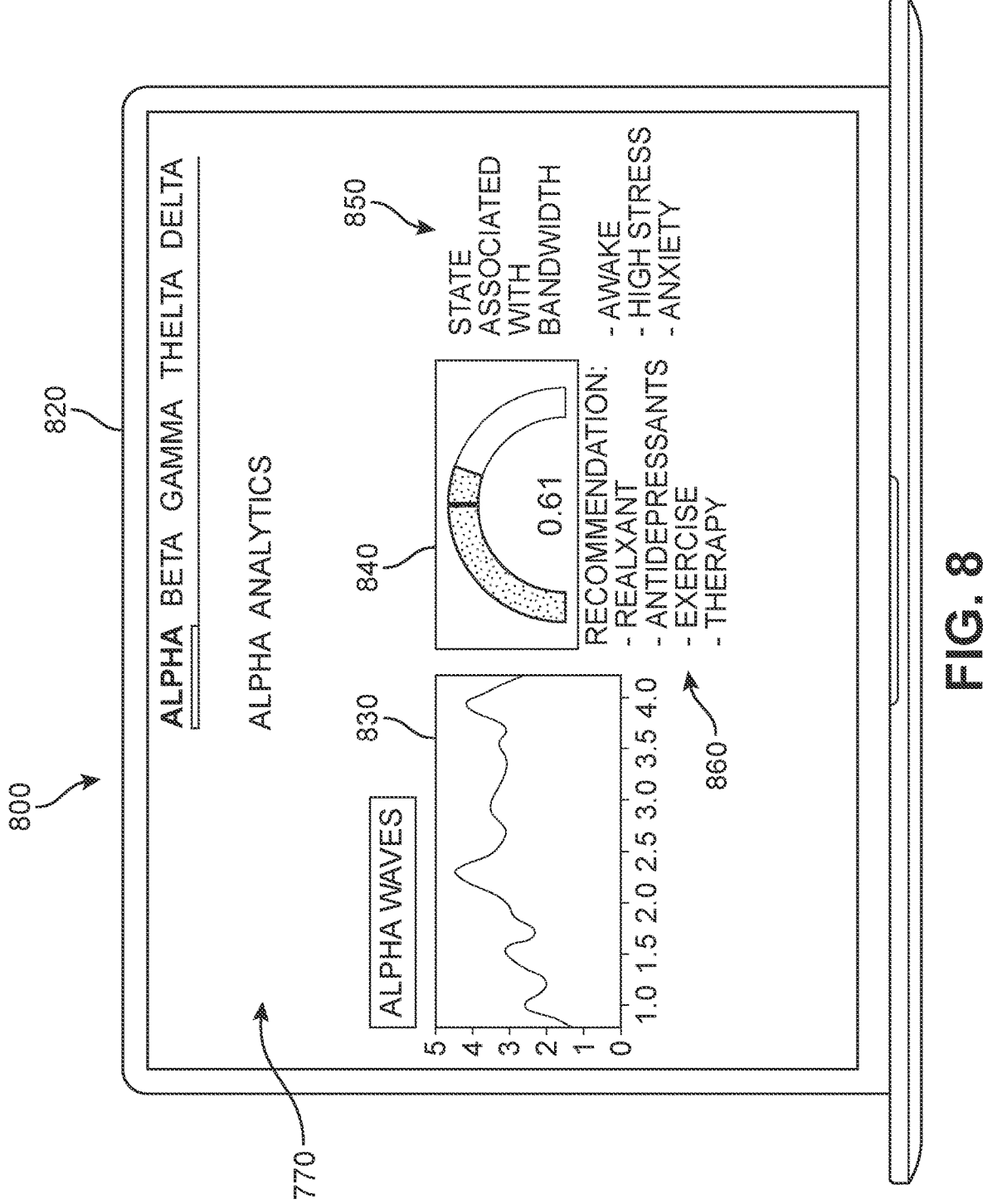
FIG. 8 is an example of a user dashboard for the brain activity interpretation system, according to an embodiment.

For purposes of illustration, a non-limiting example of the user dashboard 770 as presented via a display for a computing device 800 is shown in FIG. 8. The user dashboard 770 can be seen to include selectable tabs 820 toward the top portion of the screen, serving as a menu by which a user can quickly switch to a view of the report for each of the brain wave categories (i.e., alpha, beta, gamma, theta, delta). For this example, the alpha brainwave tab has been selected and being presented. In some embodiments, the frequency of the activity as it moves within the alpha range (i.e., 8 Hz to 12 Hz) over the course of one or multiple data collection sessions (time shown on the X axis here) can be represented graphically, as shown in a first graph 830 (e.g., a line graph or time series graph). A second graph 840 depicts the proportion of alpha waves in the user's brain activity (relative to the other frequency bands); in this case a type of meter image is used, with a line indicating the 50% mark (the meter currently showing a 0.61 alpha for the user, such that the remaining bands are less than 50%, making alpha waves the primary (dominant) brain wave type being generated by the user at this time), and the signal that potentially best characterizes the user's brain state at that time.

In different embodiments, based on the analysis of the user's alpha wave bandwidth data, the dashboard 770 can further offer insights 850 into the likely state associated with the user's brain activity (e.g., awake, high stress, anxiety), as well as intelligent recommendations 860 selected based on the likely brain state. For example, some recommendations 860 can include the user taking some type of relaxant, antidepressant, exercise, and/or therapy. In some embodiments, the recommendations may be more descriptive or detailed, indicating the specific type of exercise (e.g., walk, jog, cardio, weights, etc.) and/or therapy (e.g., cognitive behavioral therapy, dialectical behavior therapy, coaching, etc.) that would best support improved regulation of the user's brain state, or the specific prescription or over-the-counter aid that could assist the user.

Indeed, in different embodiments, model is configured to predict which or what class of neurotransmitter activity is most likely to be causing or otherwise underlying a person's dysregulation or cognitive impairments. For example, studies in humans have shown that stimulation of dopaminergic pathways may concomitantly modify attention and resting-state EEG rhythms. In healthy adults for example, treatment with the indirect dopaminergic/noradrenergic agonist methylphenidate can improve target detection by significantly reducing alpha oscillations which preceded lapses of attention. Likewise, methylphenidate has been shown to significantly suppress theta/alpha power in adults with ADHD. On the other hand, selective dopaminergic antagonists have been found to enhance alpha power and degrade cognitive performance. Moreover, a simultaneous EEG and PET study revealed endogenous striatal dopamine release to inversely correlate with power of alpha rhythms during meditation. Furthermore, dopaminergic agonists has been shown to decrease low-frequency EEG rhythms while antagonists increase them, and this has been directly linked to activation of dopamine receptors. These—and other—collective findings suggest there may be a common electrochemical mechanism linking the release of neuromodulators (such as dopamine) and the expression of low-frequency EEG rhythms (such as alpha oscillations).

In different embodiments, the information represented by the outcomes of these and other studies describing the relationship of EEG with neurotransmitter activity can be used when training the model with respect to selection of recommended actions. Thus, if the model classifies a particular bandwidth detected in a person's brain activity as "high" or "low" relative to a pre-designated threshold for that bandwidth, an analysis can also be performed by which the system determines which neurotransmitter(s) or class(es) of neurotransmitters have been known to affect EEG in a manner similar to what is being detected by the model. In response, the system can intelligently select and present one or more actions that are known to regulate the target neurotransmitter or neurotransmitter class to improve the person's condition.

As a non-limiting example, if the model determines a user is primarily exhibiting a "high alpha", the model can determine there is a higher-than-average likelihood that the levels of the neurotransmitter dopamine are insufficient, causing attention-related issues, and a dopamine agonist (or exercise/activity that is known to naturally stimulate dopamine production or dopamine receptors) may be recommended in the user's treatment, such as cardio-exercise, or stimulants like Ritalin® or Adderall®, etc. rather than a non-dopamine-based medication (such as Atomoxetine®, Clonidine®, and Guanfacine®, etc.). In another non-limiting example, the dashboard can indicate to a user that their delta frequency is non-optimal (e.g., too high or too low relative to a pre-selected threshold), and so they are strongly encouraged to rest, or listen to soothing music, or meditate, or engage in some other relaxing activity, which can further improve their productivity.

In some cases, physicians might treat patients who suffer from a neurological disorder or otherwise present with an undesirable or unwanted neurological condition with a drug regimen in an effort to modulate the behavior of the central nervous system. The physician's choice of a drug or drugs to use and the dosage of each drug may be based on prior experience with the drug(s) and dosage(s) for patients who have been diagnosed with the same disorder or who present with the same condition. Often, however, the degree to which a drug regimen is or is not effective for a particular patient may depend on factors that are specific to that patient. In some embodiments, the proposed system can offer insights into the brain activity that is specific to the individual patient. In other words, the system can reveal that two patients with the same neurological disorder or symptoms may not be equally well served by the same dose of the same drug, based in part on the recognition that each person's expression of these symptoms stem from a different neurotransmitter action. For example, a first person and a second person may present with ADHD symptoms. However, the brain activity interpretation system allows the physician to better adapt treatment. As an example, the first person's brainwaves may reflect beta waves that are too low, indicating a first type of treatment approach, while the second person's brainwaves may reflect theta waves that are too high, indicating a second, different treatment approach. Furthermore, in some embodiments, the system could be used by medical professionals to more closely monitor the efficacy of a new treatment regimen.

In different embodiments, the user dashboards associated with the system can also be referred to as action-orientated dashboards that—based on the ML model's output—enable individual end-users, family members, and care staff/personnel to monitor the user's brain state and take actions when deemed necessary by the system. In some embodiments, the dashboard can offer analytical results in the form of a report summarizing the brain states and data that was collected, and would also suggest actions that would benefit the user. Some examples of these actions/information could include (a) enabling an automated notification for taking a break or requiring longer/better rest periods (b) informing the user of their screen time and suggesting a reduction when appropriate or excessive, (c) enabling an automated screen shutdown operation when screen time exceeds a threshold (as screen time could contribute to the user's undesirable brain state), (d) tips for reducing anxiety, stress, or managing a detoxification or de-addiction process, (e) sleep assessments/healthy sleep tips, (f) instructions or guidance for pain management in real-time. In some embodiments, the analysis can be used to program an automated dispensing device for neurotransmitter blockers, enhancers, mimics, etc. (e.g., agonists and antagonists), based on the predicted brain state and corresponding analysis of neurotransmitter activity and/ or what neurotransmitters should be inhibited or increased to promote/regulate the desired brain state.

It can be appreciated that after the user has implemented one or more of the recommended beneficial actions, they may participate in another data collection session and submit new brain wave data. This data can be compared to the previous session(s)' data to determine whether the user's behavioral changes or treatments have affected the high/low amplitudes in each of the five frequency bandwidth ranges and led to an improvement in their brain state and/or reduced stress. If, for example, the delta wave frequency had been too low, the model can detect whether the delta wave frequency has shifted upward. Such personal awareness of their internal brain activity and associated analysis/symptoms can educate and motivate individuals to make changes in their lifestyle that they would not otherwise consider. When there is improvement, the dashboard can encourage the user to continue making the efforts that contributed to their better brain wave regulation.

FIG. 9 is a flow chart illustrating an embodiment of a method 900 of interpreting brain wave data for medical research, diagnosis, or behavioral therapy. The method 900 includes a first step 910 of receiving, at a brain activity interpretation system, a first electroencephalogram (EEG) recording for a first person. The EEG recording can be initially received as a raw data file that is pre-processed to extract the EEG recording. In a second step 920, the method 900 includes passing the first EEG recording as input to a machine learning model of the brain activity system, the machine learning model being trained to identify a user's brain states based on distinct bandwidths detected in EEG data. A third step 930 includes separating (and outputting), via the machine learning model, the first EEG recording into at least a first component signal falling within a first bandwidth and a second component signal falling within a second bandwidth that differs from the first bandwidth, and a fourth step 940 includes determining, at the brain activity interpretation system, the first component signal is outside of a predefined sub-range within the first bandwidth and therefore associated with a first type of brain state dysregulation. In addition, a fifth step 950 includes selecting, at the brain activity interpretation system and based on the first type of brain state dysregulation, a first beneficial action from a beneficial action repository, and a sixth step 960 includes presenting, via a dashboard for the brain activity interpretation system, the first beneficial action.

In other embodiments, the method may include additional steps or aspects. In some embodiments, the first bandwidth corresponds to a frequency range associated with one of alpha brainwaves, beta brainwaves, delta brainwaves, theta brainwaves, and gamma brainwaves. In one example, an average amplitude of the first component signal either exceeds a first threshold that lies within the first bandwidth or falls below a second threshold that lies within the first bandwidth. In another example, the method also includes automatically performing, via the brain activity interpretation system, the first beneficial action. In some cases, the first beneficial action includes playback of calming music or initiation of an audio-based guided meditation session, for example, via an app on the user's computing device. For example, the computing device providing the results of analysis of the user's measured brain activity may automatically play the calming music or audio-based guided meditation session or may automatically initiate a prompt for the user to select playing the calming music or audio-based guided meditation session. This automatic playing or prompting may be performed in response to selection of the first beneficial action. In some embodiments, the audio file selected can be pre-designated (default) by the brain activity interpretation system as a treatment or guidance targeting the specific dysregulation that was identified by the system. In another example, the audio file can be pre-selected by the user during setup or registration (or some other time) requesting this audio file be automatically opened and played in response to the system determining a particular dysregulation has been identified in their brain activity.

In different embodiments, the method can also include identifying a first neurotransmitter associated with brain waves characterized by the first component signal, where the first beneficial action promotes improved regulation of the first neurotransmitter. In some embodiments, the method also includes classifying, using the machine learning model, features of the first EEG recording into five component signals including an alpha brainwave signal, a beta brainwave signal, a delta brainwave signal, a theta brainwave signal, and a gamma brainwave signal. In one example, the method can further include determining the first component signal is the most dominant of the five component signals. In some examples, the machine learning model incorporates a gradient boosting ensemble method to classify the EEG recording. In some embodiments, selection of the first beneficial action is further based on results of a blood sample for the first person.

In another embodiment, the method can also include steps or operations of receiving, at the brain activity interpretation system, a second EEG recording for the first person after presentation of the first beneficial action; determining, at the brain activity interpretation system, the first component signal is outside of a predefined sub-range within the first bandwidth and therefore associated with a first type of brain state dysregulation; separating, using the machine learning model of the brain activity interpretation system, the EEG recording into at least a third component signal falling within the first bandwidth; determining, at the brain activity interpretation system, the third component signal is now within a predefined sub-range within the first bandwidth and therefore associated with normal brain activity; and presenting, via the dashboard, a positive feedback message including a description of the change in brain activity from the first component signal to the third component signal within the first bandwidth. For example, the dashboard may show a graph that identifies or contrasts the first component signal and the third component signal, what time/day the signals were captured, numeric data showing the difference between the signals, what symptoms (if any) the measurements for each signal reading usually correspond to, affirmation and/or encouragement of the user's engagement in their own mental health, etc.

Figure 10:
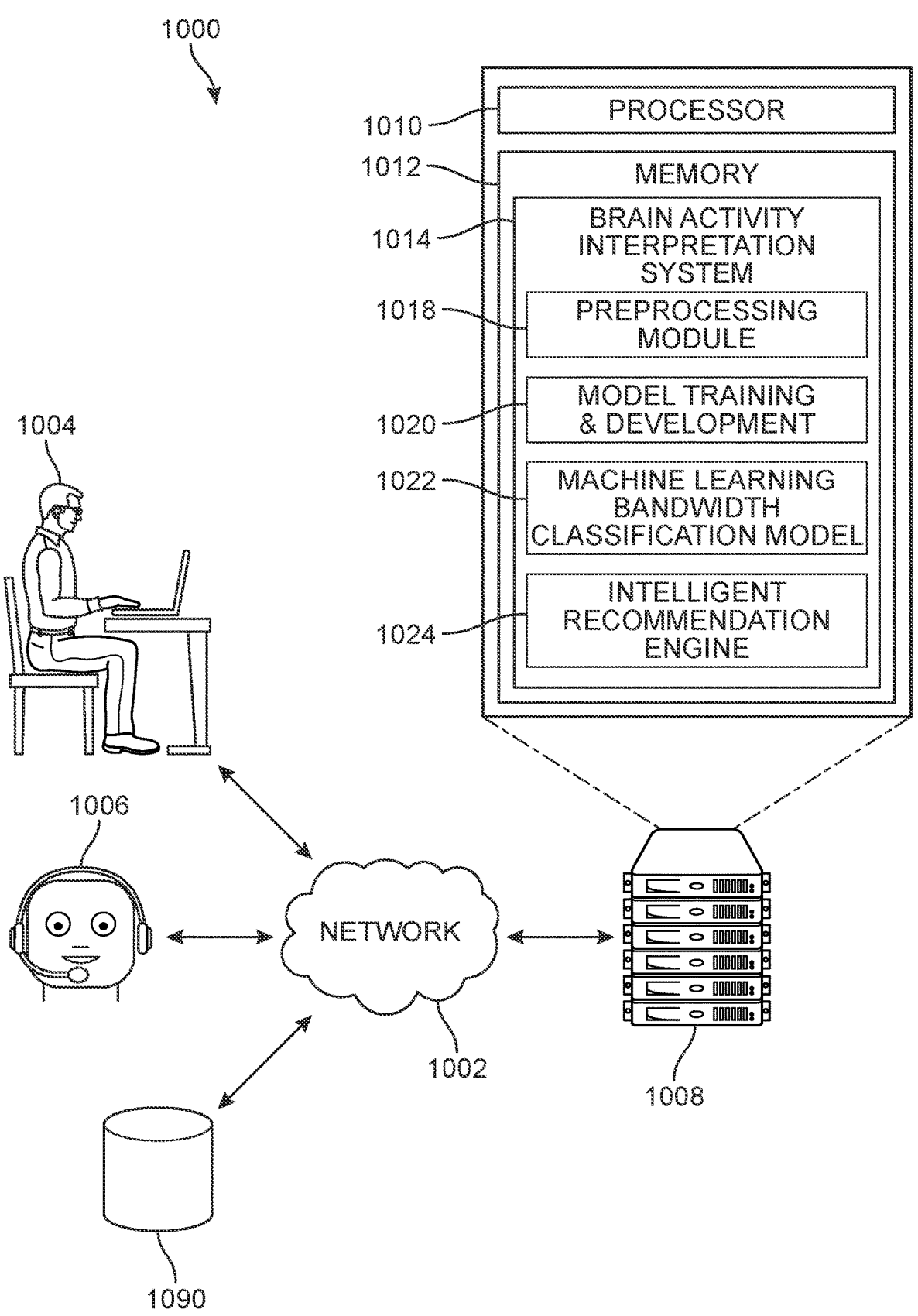
FIG. 10 is a diagram depicting example environments and components by which systems and/or methods, described herein, may be implemented.

FIG. 10 is a schematic diagram of an environment 1000 for a brain activity interpretation system 1014 ("system" 1014), according to an embodiment. The environment 1000 may include a plurality of components capable of performing the disclosed methods. For example, environment 1000 includes a user device 1004, a computing/server system 1008, and a database 1090. The components of environment 1000 can communicate with each other through a network 1002. For example, user device 1004 may retrieve information from database 1090 via network 1002. In some embodiments, network 1002 may be a wide area network ("WAN"), e.g., the Internet. In other embodiments, network 1006 may be a local area network ("LAN").

As shown in FIG. 10, components of the system 1014 may be hosted in computing system 1008, which may have a memory 1012 and a processor 1010. Processor 1010 may include a single device processor located on a single device, or it may include multiple device processors located on one or more physical devices. Memory 1012 may include any type of storage, which may be physically located on one physical device, or on multiple physical devices. In some cases, computing system 1008 may comprise one or more servers that are used to host the system.

While FIG. 10 shows one user device, it is understood that one or more user devices may be used. For example, in some embodiments, the system may include two or three user devices. In some embodiments, the user device may be a computing device used by a user. For example, user device 1004 may include a smartphone or a tablet computer. In other examples, user device 1004 may include a laptop computer, a desktop computer, and/or another type of computing device. The user devices may be used for inputting, processing, and displaying information. Referring to FIG. 10, environment 1000 may further include database 1090, which stores test data, training data, parameters and decision tree data, classification data, neurotransmitter-EEG relationship data, recommendation database (corpus) and/or other related data for the components of the system as well as other external components. This data may be retrieved by other components for system 1014. As discussed above, system 1014 may include a preprocessing module 1018, a model training and development module 1020, a machine learning bandwidth classification model 1022, and an intelligent recommendation engine 1024. Each of these components may be used to perform the operations described herein.

For purposes of this application, an "interface" may be understood to refer to a mechanism for communicating content through a client application to an application user. In some examples, interfaces may include pop-up windows that may be presented to a user via native application user interfaces (UIs), controls, actuatable interfaces, interactive buttons/options or other objects that may be shown to a user through native application UIs, as well as mechanisms that are native to a particular application for presenting associated content with those native controls. In addition, the terms "actuation" or "actuation event" refers to an event (or specific sequence of events) associated with a particular input or use of an application via an interface, which can trigger a change in the display of the application. Furthermore, a "native control" refers to a mechanism for communicating content through a client application to an application user. For example, native controls may include actuatable or selectable options or "buttons" that may be presented to a user via native application UIs, touch-screen access points, menus items, or other objects that may be shown to a user through native application UIs, segments of a larger interface, as well as mechanisms that are native to a particular application for presenting associated content with those native controls. The term "asset" refers to content that may be presented in association with a native control in a native application. As some non-limiting examples, an asset may include text in an actuatable pop-up window, audio associated with the interactive click of a button or other native application object, video associated with the user interface, or other such information presentation.

It should be understood that the text, images, and specific application features shown in the figures are for purposes of illustration only and in no way limit the manner by which the application may communicate or receive information. In addition, in other embodiments, one or more options or other fields and text may appear differently and/or may be displayed or generated anywhere else on the screen(s) associated with the client's system, including spaced apart from, adjacent to, or around the user interface. In other words, the figures present only one possible layout of the interface, and do not in any way limit the presentation arrangement of any of the disclosed features.

Embodiments may include a non-transitory computer-readable medium (CRM) storing software comprising instructions executable by one or more computers which, upon such execution, cause the one or more computers to perform the disclosed methods. Non-transitory CRM may refer to a CRM that stores data for short periods or in the presence of power such as a memory device or Random Access Memory (RAM). For example, a non-transitory computer-readable medium may include storage components, such as, a hard disk (e.g., a magnetic disk, an optical disk, a magneto-optic disk, and/or a solid state disk), a compact disc (CD), a digital versatile disc (DVD), a floppy disk, a cartridge, and/or a magnetic tape.

To provide further context, in some embodiments, some of the processes described herein can be understood to operate in a system architecture that can include a plurality of virtual local area network (VLAN) workstations at different locations that communicate with a main data center with dedicated virtual servers such as a web server for user interfaces, an app server for data processing, a database for data storage, etc. As a general matter, a virtual server is a type of virtual machine (VM) that is executed on a hardware component (e.g., server). In some examples, multiple VMs can be deployed on one or more servers.

In different embodiments, the system may be hosted at least in part in a cloud computing environment offering ready scalability and security. The cloud computing environment can include, for example, an environment that hosts the document processing management service. The cloud computing environment may provide computation, software, data access, storage, etc. services that do not require end-user knowledge of a physical location and configuration of system(s) and/or device(s) that hosts the policy management service. For example, a cloud computing environment may include a group of computing resources (referred to collectively as "computing resources" and individually as "computing resource"). It is contemplated that implementations of the present disclosure can be realized with appropriate cloud providers (e.g., AWS provided by Amazon™, GCP provided by Google™, Azure provided by Microsoft™, etc.).

The methods, devices, and processing described above may be implemented in many different ways and in many different combinations of hardware and software. For example, all or parts of the implementations may be circuitry that includes an instruction processor, such as a Central Processing Unit (CPU), microcontroller, or a microprocessor; or as an Application Specific Integrated Circuit (ASIC), Programmable Logic Device (PLD), or Field Programmable Gate Array (FPGA); or as circuitry that includes discrete logic or other circuit components, including analog circuit components, digital circuit components or both; or any combination thereof.

While various embodiments of the invention have been described, the description is intended to be exemplary, rather than limiting, and it will be apparent to those of ordinary skill in the art that many more embodiments and implementations are possible that are within the scope of the invention. Accordingly, the invention is not to be restricted except in light of the attached claims and their equivalents. Also, various modifications and changes may be made within the scope of the attached claims.

We claim:

1. A method for interpreting brain wave data for medical research, diagnosis, or behavioral therapy, the method comprising:

receiving, at a brain activity interpretation system, a first electroencephalogram (EEG) recording for a first person;

passing the first EEG recording as input to a machine learning model of the brain activity system, the machine learning model trained to identify a user's brain states based on distinct bandwidths detected in EEG data;

separating, via the machine learning model, the first EEG recording into at least a first component signal falling within a first bandwidth and a second component signal falling within a second bandwidth that differs from the first bandwidth;

determining, at the brain activity interpretation system, the first component signal is outside of a predefined sub-range, the predefined sub-range lies within the first bandwidth, and wherein the first component signal is associated with a first type of brain state dysregulation;

selecting, at the brain activity interpretation system and based on the first type of brain state dysregulation, a first action from an action repository, wherein the first action includes adjusting a nutritional intake at lunch, meditation or taking a walk after lunch, or refraining from writing emails or engaging in communications that require an emotional investment from the user;

displaying, via a dashboard for the brain activity interpretation system, the first action;

receiving, at the brain activity interpretation system, a second EEG recording for the first person after display of the first action;

determining, at the brain activity interpretation system, the first component signal is outside of a predefined sub-range, the predefined sub-range lies within the first bandwidth, and wherein the first component signal is associated with a first type of brain state dysregulation;

separating, using the machine learning model of the brain activity interpretation system, the second EEG recording into at least a third component signal, and wherein the third component signal is falling within the first bandwidth;

determining, at the brain activity interpretation system, the third component signal is within a predefined sub-range, the predefined sub-range lies within the first bandwidth, wherein the third component signal is associated with a normal brain activity, and wherein in the normal brain activity wave shapes are measured from 0.5 µV to 100 µV in amplitude peak to peak; and displaying, via the dashboard, brain wave data indicates a numerical comparison between the first component signal and third component signal, wherein the brain wave data provides instructions to the user to improve the user's mental health.

2. The method of claim 1, wherein the first bandwidth corresponds to a frequency range associated with one of alpha brainwaves, beta brainwaves, delta brainwaves, theta brainwaves, and gamma brainwaves.

3. The method of claim 1, wherein an average amplitude of the first component signal either exceeds a first threshold that lies within the first bandwidth or falls below a second threshold that lies within the first bandwidth.

4. The method of claim 1, further comprising automatically performing, via the brain activity interpretation system, the first action.

5. The method of claim 4, wherein the first action includes playback of music or initiation of an audio-based guided meditation session.

6. The method of claim 1, further comprising identifying a first neurotransmitter associated with brain waves characterized by the first component signal, wherein the first action promotes improved regulation of the first neurotransmitter.

7. The method of claim 1, further comprising classifying, using the machine learning model, features of the first EEG recording into five component signals including an alpha brainwave signal, a beta brainwave signal, a delta brainwave signal, a theta brainwave signal, and a gamma brainwave signal.

8. The method of claim 7, further comprising determining the first component signal is the most dominant of the five component signals.

9. The method of claim 7, wherein the machine learning model incorporates a gradient boosting ensemble method to classify the EEG recording.

10. A non-transitory computer-readable medium storing software comprising instructions executable by one or more computers which, upon such execution, cause the one or more computers to interpret brain wave data for medical research, diagnosis, or behavioral therapy by performing the following:

receive, at a brain activity interpretation system, a first electroencephalogram (EEG) recording for a first person;

pass the first EEG recording as input to a machine learning model of the brain activity system, the machine learning model trained to identify a user's brain states based on distinct bandwidths detected in EEG data;

separate, via the machine learning model, the first EEG recording into at least a first component signal falling within a first bandwidth and a second component signal falling within a second bandwidth that differs from the first bandwidth;

determine, at the brain activity interpretation system, the first component signal is outside of a predefined sub-range, the predefined sub-range lies within the first bandwidth, and wherein the first component signal is associated with a first type of brain state dysregulation;

select, at the brain activity interpretation system and based on the first type of brain state dysregulation, a first action from an action repository, wherein the first action includes adjusting their nutritional intake at lunch, meditation or taking a walk after lunch, or refraining from writing emails or engaging in communications that require an emotional investment from the user;

display, via a dashboard for the brain activity interpretation system, the first action;

receive, at the brain activity interpretation system, a second EEG recording for the first person after display of the first action;

determine, at the brain activity interpretation system, the first component signal is outside of a predefined sub-range, the pre-defined sub-range lies within the first bandwidth, and wherein the first component signal is associated with a first type of brain state dysregulation;

separate, using the machine learning model of the brain activity interpretation system, the second EEG recording into at least a third component signal, and wherein the third component signal falling within the first bandwidth;

determine, at the brain activity interpretation system, the third component signal is within a predefined sub-range, the predefined sub-range lies within the first bandwidth, wherein the third component signal is associated with a normal brain activity, and wherein in the normal brain activity wave shapes are measured from 0.5 µV to 100 µV in amplitude peak to peak; and display, via the dashboard, brain wave data indicates a numerical comparison between the first component signal and third component signal, wherein the brain wave data provides instructions to the user to improve the user's mental health.

11. The non-transitory computer-readable medium storing software of claim 10, wherein the first bandwidth corresponds to a frequency range associated with one of alpha brainwaves, beta brainwaves, delta brainwaves, theta brainwaves, and gamma brainwaves.

12. The non-transitory computer-readable medium storing software of claim 10, wherein an average amplitude of the first component signal either exceeds a first threshold that lies within the first bandwidth or falls below a second threshold that lies within the first bandwidth.

13. The non-transitory computer-readable medium storing software of claim 10, wherein the instructions further cause the one or more computers to automatically perform, via the brain activity interpretation system, the first action.

14. The non-transitory computer-readable medium storing software of claim 10, wherein the first action includes playback of music or initiation of an audio-based guided meditation session.

15. A system for interpreting brain wave data for medical research, diagnosis, or behavioral therapy, the system comprising one or more computers and one or more storage devices storing instructions that are operable, when executed by the one or more computers, to cause the one or more computers to:

receive, at a brain activity interpretation system, a first electroencephalogram (EEG) recording for a first person;

pass the first EEG recording as input to a machine learning model of the brain activity system, the machine learning model trained to identify a user's brain states based on distinct bandwidths detected in EEG data;

separate, via the machine learning model, the first EEG recording into at least a first component signal falling within a first bandwidth and a second component signal falling within a second bandwidth that differs from the first bandwidth;

determine, at the brain activity interpretation system, the first component signal is outside of a predefined sub-range, the predefined sub-range lies within the first bandwidth, and wherein the first component signal is associated with a first type of brain state dysregulation;

select, at the brain activity interpretation system and based on the first type of brain state dysregulation, a first action from a action repository, wherein the first action includes adjusting a nutritional intake at lunch, meditation or taking a walk after lunch, or refraining from writing emails or engaging in communications that require an emotional investment from the user;

display, via a dashboard for the brain activity interpretation system, the first action;

receive, at the brain activity interpretation system, a second EEG recording for the first person after display of the first action;

determine, at the brain activity interpretation system, the first component signal is outside of a predefined sub-range, the predefined sub-range lies within the first bandwidth, and wherein the first component signal is associated with a first type of brain state dysregulation;

separate using the machine learning model of the brain activity interpretation system, the second EEG recording into at least a third component signal, and wherein the third component signal is falling within the first bandwidth;

determine, at the brain activity interpretation system, the third component signal is within a predefined sub-range, the predefined sub-range lies within the first bandwidth, wherein the third component signal is associated with a normal brain activity, and wherein in the normal brain activity wave shapes are measured from 0.5 µV to 100 µV in amplitude peak to peak; and display, via the dashboard, brain wave data indicates a numerical comparison between the first component signal and third component signal, wherein the brain wave data provides instructions to the user to improve the user's mental health.

16. The system of claim 15, wherein the instructions further cause the one or more computers to classify, using the machine learning model, features of the EEG recording into five component signals including an alpha brainwave signal, a beta brainwave signal, a delta brainwave signal, a theta brainwave signal, and a gamma brainwave signal.

17. The system of claim 16, wherein the instructions further cause the one or more computers to determine the first component signal is the most dominant of the five component signals.

18. The system of claim 16, wherein the machine learning model incorporates a gradient boosting ensemble method to classify the EEG recording.

* * * * *